US009421356B2

(12) United States Patent
Anderson et al.

(10) Patent No.: US 9,421,356 B2
(45) Date of Patent: Aug. 23, 2016

(54) TRANSDERMAL METHODS AND SYSTEMS FOR THE DELIVERY OF CORTICOSTEROID COMPOUNDS

(75) Inventors: Carter R. Anderson, Inver Grove Heights, MN (US); Russell L. Morris, Lindstrom, MN (US); Robert Cohen, Eden Prairie, MN (US); William V. Fowler, Minneapolis, MN (US)

(73) Assignee: Teikoku Pharma USA, Inc., San Jose, CA (US)

( * ) Notice: Subject to any disclaimer, the term of this patent is extended or adjusted under 35 U.S.C. 154(b) by 636 days.

(21) Appl. No.: 12/199,051

(22) Filed: Aug. 27, 2008

(65) Prior Publication Data
US 2009/0062720 A1     Mar. 5, 2009

Related U.S. Application Data

(60) Provisional application No. 60/968,380, filed on Aug. 28, 2007.

(51) Int. Cl.
*A61N 1/04*     (2006.01)
*A61K 9/00*     (2006.01)

(52) U.S. Cl.
CPC ............ *A61N 1/0448* (2013.01); *A61K 9/0009* (2013.01); *A61N 1/044* (2013.01)

(58) Field of Classification Search
CPC ... A61K 9/0009; A61N 1/0448; A61N 1/044; A61M 5/14248; A61M 35/00; A61M 2205/0272; A61M 5/14244; A61M 2037/0007; A61M 37/0092
USPC ...................... 604/20; 424/449, 435
See application file for complete search history.

(56) References Cited

U.S. PATENT DOCUMENTS

| | | | | |
|---|---|---|---|---|
| 5,049,387 | A | * | 9/1991 | Amkraut ........................ 424/435 |
| 5,582,587 | A | * | 12/1996 | Gyory et al. ..................... 604/20 |
| 6,324,424 | B1 | * | 11/2001 | Ledger et al. ................... 604/20 |
| 2003/0028170 | A1 | * | 2/2003 | Anderson et al. ............. 604/501 |
| 2003/0167073 | A1 | * | 9/2003 | Nakamura et al. ................ 607/2 |
| 2006/0067936 | A1 | * | 3/2006 | Benson et al. ............. 424/145.1 |

OTHER PUBLICATIONS

Craig Banta, Jom, A Prospective, *Nonrandomized Study of Iontophoresis, Wrist Splinting, and Antiinflammatory Medication in the Treatment of Early-Mild Carpal Tunnel Syndrome*, vol. 36, No. 2, Feb. 1994, pp. 166-168.

Anderson et al, International Journal of Pharmaceutical Compounding, *Quantification of Total Dexamethasone Phosphate Delivery by Iontophoresis*, vol. 7, No. 2, Mar./Apr. 2003, pp. 155-159.

Anderson et al, Physical Therapy, *Effects of Iontophoresis Current Magnitude and Duration on Dexamethoasone Deposition and Localized Drug Retention*, vol. 83, No. 2, Feb. 2003, pp. 161-170.

(Continued)

*Primary Examiner* — Aarti B Berdichevsky
*Assistant Examiner* — Brandy S Lee
(74) *Attorney, Agent, or Firm* — Baker & Hostetler LLP

(57) ABSTRACT

An integrated iontophoresis skin-worn patch and method for delivering a therapeutically effective amount of a corticosteroid drug compound in a systemically-safe and skin-safe manner for site-specific treatment of inflammation pain is disclosed.

36 Claims, 5 Drawing Sheets

(56) References Cited

OTHER PUBLICATIONS

Phil R. Harris, Journal of Orthopedic and Sports Physical Therapy, *Iontophoresis: Clinical Research in Musculoskeletal Inflammaotry Conditions*, vol. 4, No. 2, 1982, pp. 109-112.

Glass et al, International Journal of Dermatology, *The Quantity and Distribution of Radiolabeled Dexamethasone Delivered to Tissue by Iontophoresis*, vol. 19, Nov. 1980, pp. 519-525.

Gudeman et al, American Journal of Sports Medicine, *Treatment of Plantar Fasciitis by Iontophoresis of 0.4& Dexamethasone*, vol. 25, No. 3, 1997, pp. 312-316.

Martin et al, Southern Medical Journal, *Effect of Injected Versus Iontophoretic Corticosteroid on the Rabbit Tendon*, vol. 92, No. 6, Jun. 1999, pp. 600-608.

Hasson et al, Physiotherapy Canada, *Exercise Training and Dexamethasone Iontophoresis in Rheumatoid Arthritis*, vol. 43, No. 2, Apr. 1991, pp. 11-14.

IOMED Inc—IOX Unscheduled Material Events (80K) Exhibit 99, May 1, 2001 http://sec.edgar-online.com/2001/05/03/0001020488-01-500011/Section_4.asp.

Perlik et al, Eastern Orthopedic Assoc./Southern Orthopedic Assoc. Annual Meeting, Dublin, Ireland, *A Double Blinded, Randomized, Placebo-Controlled Clinical Trial Evaluating the Effectiveness of the IontoPatch Using Dexamethasone Sodium Phosphate to Treat Lateral Epicondylitis*, Jul. 30-Aug. 3, 2003.

Murray et al, Journal of the APTA, *The Iontophoresis of $C_{21}$ Esterified Glucocorticoids: Preliminary Report*, vol. 43, No. 8, Aug. 1963, pp. 579-563.

Nirschl et al, American Journal of Sports Medicine, *Iontophoretic Administration of Dexamethasone Sodium Phosphate for Acute Epicondylitis*, vol. 31, No. 2, 2003, pp. 189-195.

Sylvestre et al, Physical Therapy, *In Vitro Optimization of Dexamethasone Phosphate Delivery by Iontophoresis*, vol. 88, No. 10, Oct. 2008, pp. 1177-1187.

Petelenz et al, Journal of Controlled Release, *Iontophoresis of Dexamethasone: Laboratory Studies*, vol. 20, 1992, pp. 55-66.

Runeson & Haker, Scandinavian Journal of Medicine & Science in Sports, *Iontophoresis with Cortisone in the Treatment of Lateral Epicondylalgia (Tennis Elbow)—a Double-Blind Study*, vol. 12, 2002, pp. 136-142.

Gurney et al, American Journal of Sports Medicine, *Absorption of Dexaqmethasone Sodium Phosphate in Human Connective Tissue Using Iontophoresis*, vol. X, No. X, Jan. 11, 2008, pp. 1-7.

\* cited by examiner

TRANSDERMAL METHODS AND SYSTEMS FOR THE DELIVERY OF CORTICOSTEROID COMPOUNDS

CROSS-REFERENCED TO RELATED APPLICATIONS

This application is a non-provisional application of Application No. 60/968,380, filed Aug. 28, 2007 and claims priority from that application which is also deemed incorporated by reference in its entirety in this application.

STATEMENT REGARDING FEDERALLY SPONSORED RESEARCH OR DEVELOPMENT

Not applicable

BACKGROUND OF THE INVENTION

I. Field of the Invention

The present invention is related generally to transdermal delivery of active compounds by iontophoresis. Specifically, this invention relates to a method and system for the transdermal delivery of corticosteroid drug compounds, particularly in water-soluble sodium salt forms including dexamethasone sodium phosphate and betamethasone sodium phosphate. Further, this invention provides a wearable iontophoresis system, which can be used to provide both rapid pain relief and sustained action for the prevention of pain recurrence.

II. Related Art

The process of iontophoresis was first described by LeDuc in 1908 and has since found wide commercial use in the delivery of ionically charged therapeutic agent molecules such as pilocarpine, lidocaine and dexamethasone across the skin of patients using an electromotive force. In this delivery method, ions bearing a positive charge are driven across the skin at the site of an electrolytic electrical system anode while ions bearing a negative charge are driven across the skin at the site of an electrolytic system cathode.

Generally, early iontophoretic devices included two electrodes attached by adhesive materials to a patient, each connected by a wire to a remote power supply, generally a microprocessor-controlled electrical instrument. While some may still be in use, more recently, self-contained wearable iontophoretic systems have been developed. These systems also include two electrodes fixed to patients by means of adhesive materials; however, they do not require external wires and are much smaller in size.

Generally, iontophoresis systems can be either voltage or current regulated. Voltage regulated designs are generally less complex and less costly to manufacture. With a voltage regulated design, the time required to deliver a full dose may vary significantly from patient to patient, because differences in skin resistance will cause differences in delivery current. Because of this, all patients may be forced to wear a patch for a longer time to compensate for the possibility of high skin resistance. This can also be a safety concern, as patients having relatively low skin resistance may experience higher than desirable currents that can cause skin irritation and/or allow the delivery of higher than desirable dosage rates to the systemic circulation of a patient. Current regulated systems, on the other hand, while more complex and costly to manufacture, enable a more consistent delivery rate that is less affected by variability in skin resistance. Thus, current regulated systems are generally more desirable.

It follows that subject skin safety provides a significant limitation to the use of iontophoresis. High levels of current and prolonged administration are considered to be undesirable, and include the possibility of skin burns. Additionally, introduction of drug or formulation excipients into the skin can produce irritation, sensitization, or cause other compound related adverse effects. In the case of topical corticosteroids, the Physicians' Desk Reference (PDR) lists drug-related adverse effects including (in decreasing order of occurrence): burning, itching, irritation, dryness, folliculitis, hypertrichosis, and others. Electrode dimensions for iontophoresis in a delivery pad preferably should be relatively large in area in order to enhance relatively even distribution of current and minimize the possibility of any locally high skin current density.

Delivery of dexamethasone by iontophoresis is now commonly used in physical therapy clinics for treatment of inflammation, and was first reported in 1963 by Murray et al (Journal of the APTA, Vol. 43 No 8 August 1963 pp 579-581). Typically, this is accomplished by loading dry electrode chambers with separately obtained aqueous solutions of dexamethasone sodium phosphate and saline, followed by an iontophoretic skin patch application to the patient in the clinic. In general, a course of treatment consists of up to six separate iontophoresis applications. The need for multiple applications represents an inconvenience to clinicians and patients, as patients must return to a clinic for each application.

Current systems available for dexamethasone iontophoresis involve loading a 4 mg/ml free-flowing liquid solution of dexamethasone into a patch at the time of use and an iontophoretic charge dosage of between 40 and 80 mA-minutes is typically applied thereafter. Estimates of the amount of dexamethasone delivered in this cycle have ranged from 10 micrograms (see Petelenz, Journal of Controlled Release, 20 (1992) pp 55-66) to 1.4 milligrams (Journal of Pharmaceutical Compounding Vol. 7 No 2 March/April 2003 pp 155-159). The need to obtain and load a separate solution of dexamethasone, of course, represents an inconvenience to clinicians and patients. Moreover, the necessity of adding the dexamethasone as a free-flowing liquid introduces a potential for overfilling, under-filling, or misdirection of dexamethasone solution into the reservoir. Liquids can also flow among the chambers of the patch while the patch is worn, which can alter the direction of current flow, cause adhesion failure, or even be lost from the patch with body movement.

A number of small clinical trials have also demonstrated that this dexamethasone iontophoresis process can be clinically effective. References regarding some of these are listed in Appendix A.

Others have reported a failure to demonstrate clinical efficacy with dexamethasone iontophoresis. See, for example, Runeson L, Haker E: Iontophoresis with cortisone in the treatment of lateral epicondylalgia (tennis elbow)—a double blind study (Scand J Med Sci Sports: 136-142, 2002).

Notably, a relatively recent attempt to confirm efficacy of dexamethasone iontophoresis in a large scale FDA phase III clinical trial failed to confirm effectiveness (Iomed, Inc., Salt Lake City, Press release May 1, 2001). Thus, despite 40 years of use, the evidence for clinical effectiveness of dexamethasone iontophoresis is considered anecdotal and, to date, the FDA has not authorized dexamethasone to be labeled for iontophoretic delivery or marketed in a co-packaged combination iontophoresis product.

Also of note is the fact that to date all known, previous attempts to measure efficacy of corticosteroid iontophoresis are based on clinician-applied devices. Clinicians are believed to be better trained to properly load the drug into the chamber and position the electrodes on the patient body, which can be very difficult for the patient to do in places not easily seen and/or accessible to the patient with both hands. If the electrodes of these previous devices are not properly placed on the body, there remains a possibility that the current may be concentrated only in reduced areas of good contact and this can lead to potential for skin damage. While advantages to having clinicians load and apply these devices exist, as indicated, the fact that patients must return to a clinic for each application represents a significant inconvenience.

With administration of corticosteroids, an important safety concern also relates to the amount of the compound released to the systemic blood circulation. Short term side effects associated with systemic corticosteroids include sleep disturbances, weight gain, and psychological effects. Longer term side effects include hypopituitary-adrenal-axis suppression, osteoporosis, muscle weakness, aggravation of diabetes mellitus, and others. Therefore, with delivery of corticosteroids by iontophoresis, it is of paramount safety concern to use conditions which minimize the release to systemic blood circulation.

To date, most clinical uses involving dexamethasone iontophoresis involve delivery devices with adjustable settings for current level and current duration time, but the clinician administering the iontophoresis does not have any knowledge as to whether the conditions selected facilitate release of corticosteroid to systemic blood circulation. In fact, a clinician desiring to improve clinical efficacy of iontophoresis will likely increase the current level and/or duration, unknowingly subjecting the patient to potentially increased dangers of systemic release of the corticosteroids.

Therefore, a need exists for a more clinically effective, skin-safe, systemically-safe and convenient iontophoretic delivery system for corticosteroids that enables delivery of a therapeutically effective amount in a relatively short time.

SUMMARY OF THE INVENTION

The present invention provides a system for the safe delivery of a therapeutically effective site-specific dosage of a corticosteroid to treat site specific inflammatory pain. The system uses a self-contained skin-applied patch which includes a suitable amount of the corticosteroid to be delivered in a compatible form. The skin-applied patch is preferably a single-use, disposable device that provides for a continuous release of a corticosteroid when applied directly over an area of inflammation on the body. Generally, the patch of the invention is capable of delivering a total amount of corticosteroid that is greater than 1 milligram on average, and which is delivered at a generally constant and non-adjustable rate which preserves safe skin conditions over a period of time from about 6 to as much as 20 hours or more. Further, it has been found that use of the patch will not result in release of corticosteroid to the systemic blood circulation to any significant degree. Thus, the present invention provides a patch delivery system that is clinically effective, user convenient, and delivery is accomplished under skin-safe conditions.

As indicated, preferably, the delivery is enhanced by iontophoresis, and the corticosteroid is provided in a water-soluble, salt form formulation in a reservoir in an iontophoretic patch. The concentration of the corticosteroid in the reservoir of the patch preferably exceeds 4 mg/ml. Most preferably, the concentration of corticosteroid in the reservoir of the patch is approximately 10 mg/ml. The corticosteroid solution should be formulated with minimal presence of competing ions of similar charge to the salt used which may be, for example, dexamethasone sodium phosphate.

Also preferably, the formulation of the corticosteroid is in a pre-packaged viscous aqueous gel form of a generally defined shape and thickness, e.g. it is not added to the patch as a free-flowing liquid. The gels are preferably formulated with a viscosity range preferably between 8,000-120,000 centipoise, but this is not limited so long as the gel retains shape to be successfully assembled in the patch. The gel is preferably carried by an absorbent pad.

The substances applied in accordance with the invention are for site-specific treatment of inflammation. Preferably, the total skin-contact delivery area for the corticosteroid gel is between 8 and 16 $cm^2$, and most preferably between 10 and 14 $cm^2$. The total charge dose to be administered in a single application preferably exceeds 80 mAmin.

BRIEF DESCRIPTION OF THE DRAWINGS

In the drawings, wherein like reference characters denote like parts throughout the same.

DETAILED DESCRIPTION

Figure 1A:
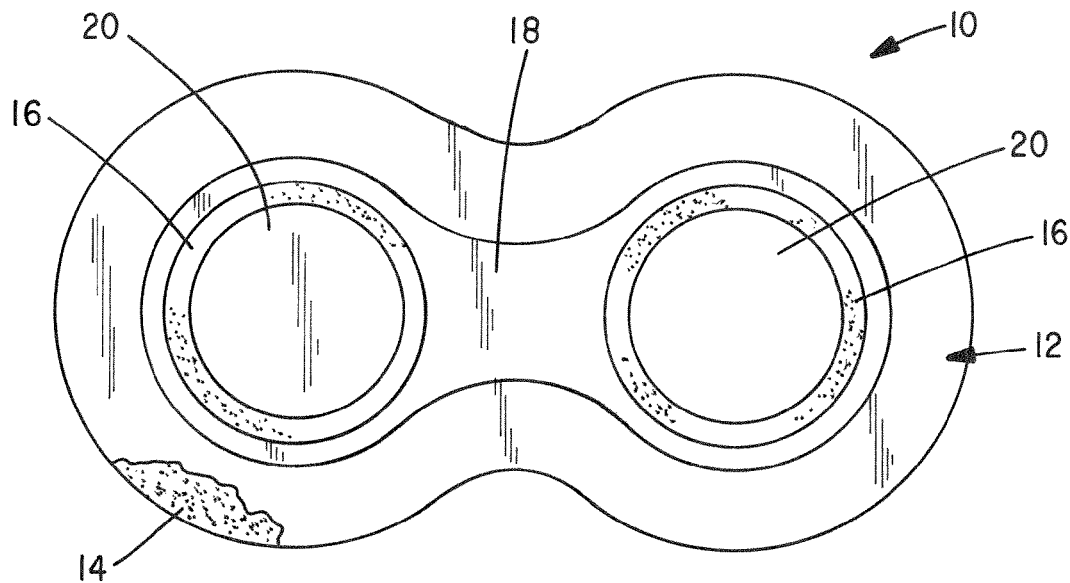
FIG. 1a is a schematic view of a possible assembled iontophoretic transdermal patch for use in accordance with the invention as viewed from the side to be applied to the skin with a protective or release packaging layer partially removed for clarity.
Figure 1B:
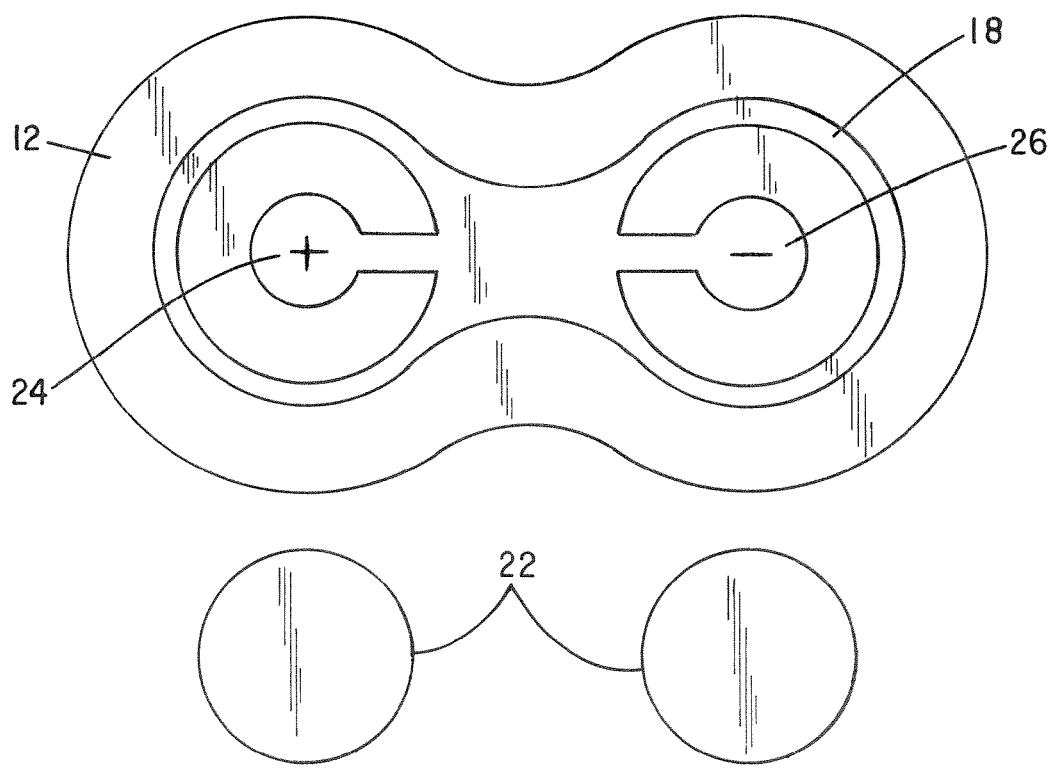
FIG. 1b is a schematic view similar to FIG. 1a with the absorbent hydrogel pads removed exposing the electrodes of the patch.
Figure 1C:
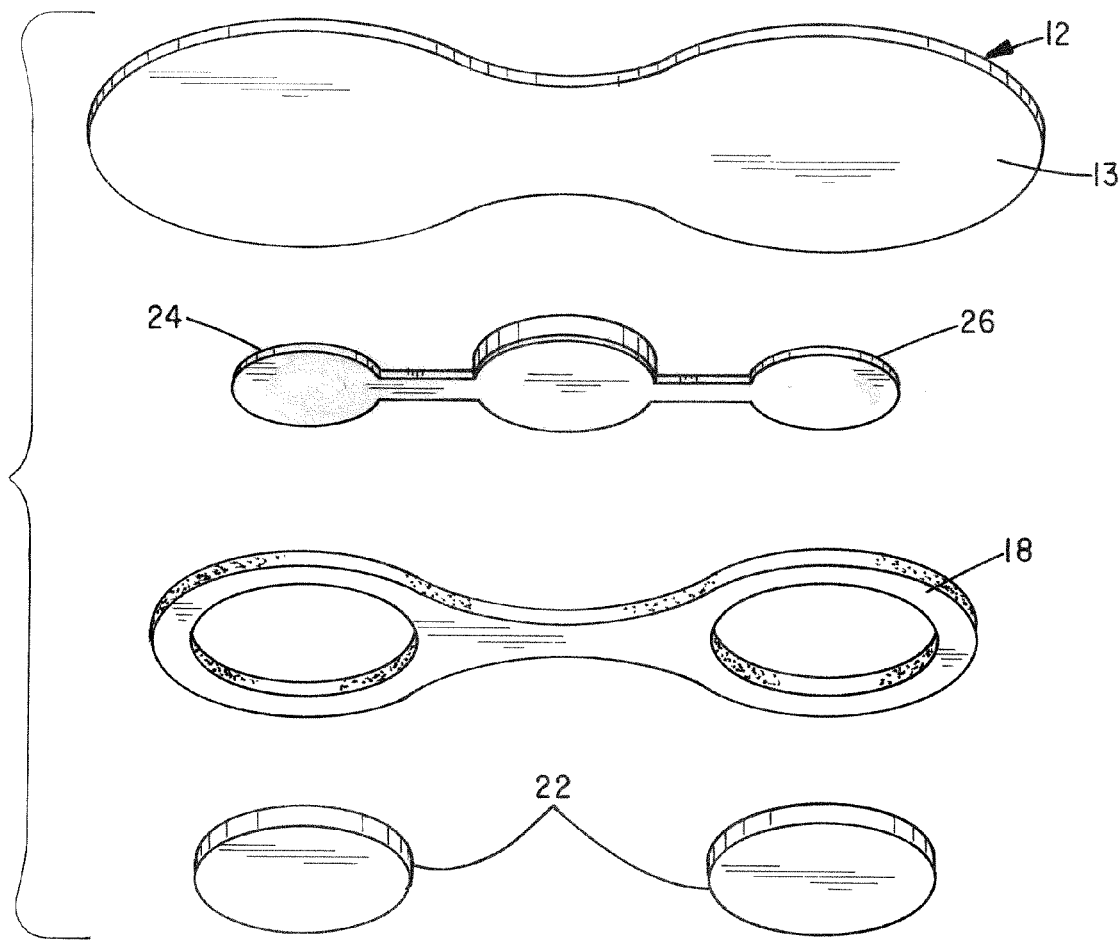
FIG. 1c is a schematic exploded view of the iontophoretic transdermal patch of FIGS. 1a and 1b.

The following description includes detailed information regarding certain embodiments of the present invention. These are presented as examples of inventive concepts rather than as limitations on them. Other embodiments, variations and combinations as will occur to those skilled in the art are also contemplated to be within the scope of the invention.

1. Definitions

In addition to any terms defined elsewhere used in the present application, the following definitions apply to usage of certain terms in this application.

The term "integrated" means completely self-contained and defines patches which contain the drug, power source, and all other necessary components to deliver the drug iontophoretically in a single wearable patch. The term "integrated", thus, denotes patches which do not require a separate power source or controller.

The term "iontophoretic transdermal patch" as used herein includes integrated devices which promote the administration of therapeutic compounds through the skin by using electrical current to promote the absorption of the compound from the patch through the skin of the subject.

The term "therapeutic compounds of interest" means corticosteroid compounds in any form suitable for transdermal administration using iontophoresis.

The term "combination device" means an iontophoretic patch specifically designed and intended for delivery of corticosteroid and which is co-packaged or co-promoted with the corticosteroid drug substance and sold as a system intended only for delivery of that corticosteroid. Importantly, delivery parameters such as current level, drug selection, drug concentration, etc., which may affect the safety or efficacy of the device, are fixed and cannot be altered by the user.

The terms "does not substantially irritate a subject's skin", or "skin-safe" as used herein, is meant to include patches which result in a skin erythema score of 2.50 or less, more preferably 2.00 or less, or most preferably 1.00 or less about two hours after patch removal. In this scoring system, 0=no erythema, 1=very slight erythema (barely perceptible), 2=well defined erythema, 3=moderate to severe erythema, 4=sever erythema to slight eschar formation.

The term "systemically safe", as used herein, is meant to include patches where release of corticosteroid to the systemic blood circulation is less than 10% of that released by a 6 mg subcutaneous injection, as measured by the maximum concentration found in the systemic blood supply (Cmax).

The term "to deliver" is used to represent the total amount of compound released from the patch to the skin during the wear period, and is an amount greater than the total amount of compound that reaches the systemic blood circulation. The amount delivered is usually measured by comparison of the amount of compound initially loaded into a patch to the final contents of the patch following removal from the body.

The term "clinically effective" is used to represent a patch designed to deliver at least 1 mg of corticosteroid without substantially irritating the subject's skin. An iontophoretic charge dose of 60 mA-minutes or more is generally required to deliver this dosage.

The term "formulated corticosteroid" is used to represent a corticosteroid solution that is specifically designed for use in a transdermal patch.

The term "shelf life" includes the period of time that the combination device can rest unused in ambient temperature and moisture levels and still be used to perform its intended function, e.g., administer the desired compounds to treat a subject.

2. Patches of the Invention

The patches of the invention are preferably self-contained with respect to delivery of a corticosteroid drug substance of interest in any form suitable for transdermal administration. The patches are preferably ones that deliver the corticosteroid compounds using iontophoresis and, most preferably, integrated or combination devices which need only be removed from packaging and applied to the skin where localized treatment is needed. Application to the skin completes the circuit and the device begins to administer the therapeutic compound immediately. Preferably, the duration of time necessary to complete a clinically effective dose is between about 6 and about 20 hours, more preferably this time is between 6 and 12 hours, and most preferably, this time is between 8 and 10 hours.

One embodiment of a patch suitable for delivery of the corticosteroid drug substance in accordance with the invention is shown generally at 10 in FIGS. 1a-1d and includes an impervious, non-conducting flexible backing layer 12 which may include a peelable release layer 13 and which has a peripheral adhesive pattern applied to the inner surface beneath the release layer (shown partially at 14) suitable for application to the skin of a patient in a manner which also prevents leakage of any materials beyond the adhesive border.

A pair of narrow rings of adhesive are also shown at 16 within a foam barrier 18 which defines recessed areas 20 adapted to receive absorbent hydrogel-containing gel pads 22 (FIG. 1b) which are designed to absorb and carry an amount of a hydrogel material which may, in turn, contain a therapeutic compound of interest to be administered, shown removed revealing two electrodes. Gel pads usable in the patch of the invention are described in greater detail in connection with FIGS. 3a and 3b, below. A power source anode is shown at 24 and a power source cathode at 26. While it will be appreciated that many materials can be used in accordance with iontophoretic art, the power source anode 24 may preferably include a layer of zinc printed on a silver conductor. The cathode, of course, must be compatible with the anode and, in the same embodiment, is preferably silver or silver chloride printed on the silver conductor. One of the absorbent gel-containing pads 22 is associated with and in electrical communication with each electrode. One gel pad is used for containing or retaining the therapeutic compound of interest to be administered and a corresponding conductor material is contained in the other gel pad to enable the circuit to be completed at the time the patch is applied to the skin.

It should be noted that whether the pad containing material to be administered is associated with the anode or the cathode depends on the charge of the material itself. Accordingly, the corticosteroid salt materials administered in accordance with the present invention are administered from the pad 22 associated with the power source cathode 26. The gel pad 22 associated with the anode 24 is imbibed with unmedicated conductive gel material. As indicated, recesses 22 in the patch for receiving and containing the absorbent gel pads are provided as by a shaped foam barrier 18, as shown in the figures.

Figure 1D:
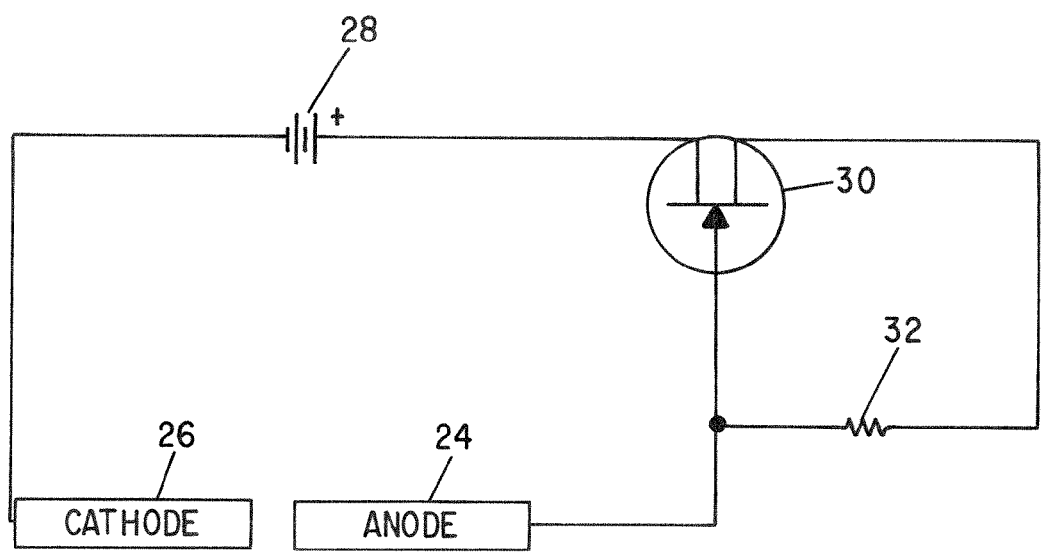
FIG. 1d is a schematic diagram of an iontophoresis circuit suitable for use in the transdermal patch of FIGS. 1a-1c.
Figure 2:
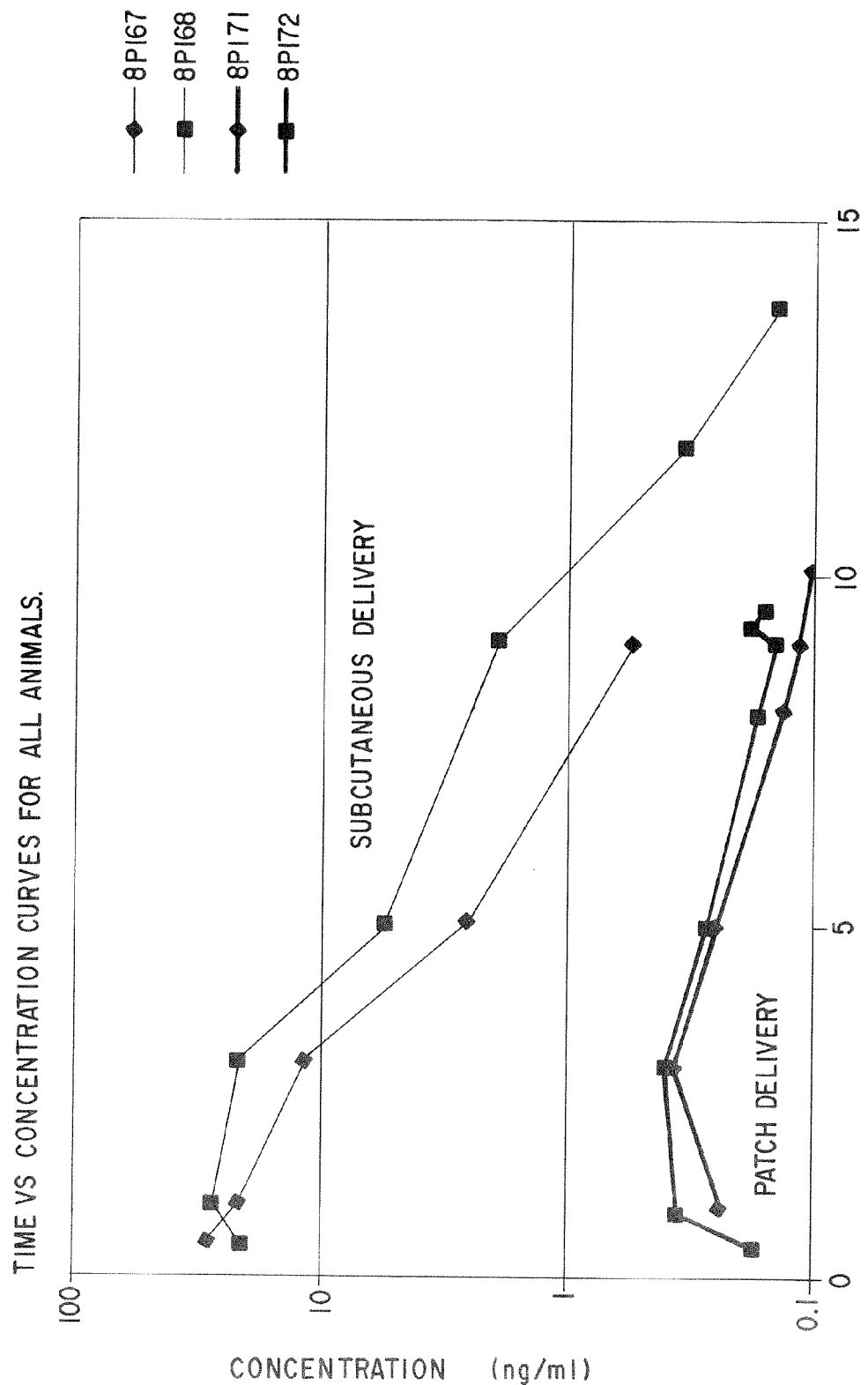
FIG. 2 is a graphical representation of time vs. concentration of corticosteroid found in the systemic blood supply of four test animals of Example 1.

In accordance with embodiments of the patch of the present invention, additional circuit components can be optionally incorporated in the circuitry to control current delivery in a well known manner. An example of circuitry that can produce controlled currents is shown in FIG. 1d and includes a voltage source such as one or more lithium button cells as at 28 in series connection with one or more transistors 30 and the circuit may include resisters as at 32. These and other circuit configurations can be used to provide current control and are generally well known to those skilled in the art.

Figure 3A:
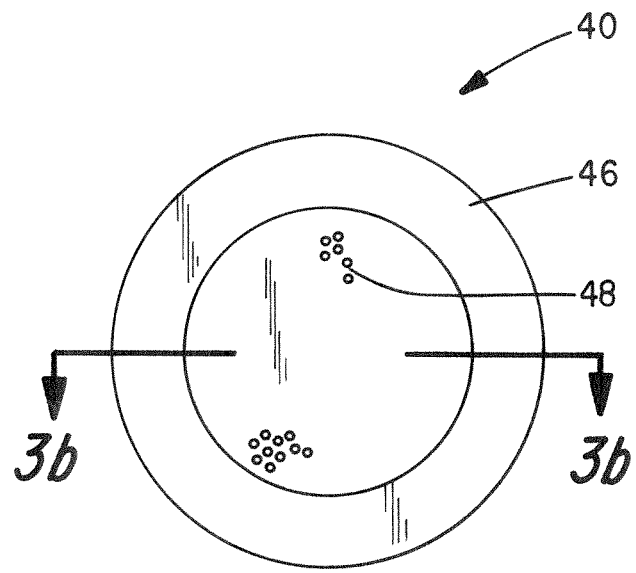
FIGS. 3a and 3b are top and cross-sectional views, respectively, of an absorbent pad usable in the patch of the invention.
Figure 3B:
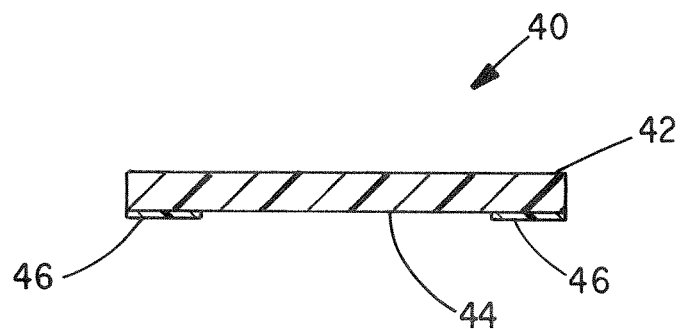

FIGS. 3a and 3b show top and side cross-sectional views, respectively, illustrating the structure of one embodiment of a composite pad suitable for use in the patch of the invention at 40. As indicated, the anode and cathode pad composite materials are preferably of a non-woven structure to maintain the continuity of drug-containing hydrogel material in the structure and may include a plurality of layers, possibly up to three layers, of material. Examples of materials that may be suitable for the absorbent non-woven matrix include cotton, polypropylene, polyethylene, and polyester. Most preferably, the absorbent material is polypropylene. One example of an embodiment includes a thick needle-punched polypropylene layer 42, a thin, permeable polyethylene net layer 44, and a thin, occlusive peripheral polypropylene layer 46. The layers may be heat fused together without requiring adhesives. All three layers are cut to have the same outside perimeter shape. The occlusive layer 46 is cut to the shape of a perimeter ring that remains intact and occlusive. Inside the ring, the occlusive layer 46 is cut out completely or perforated so that the inside region 48 becomes permeable. The permeable region 48 is shaped to coincide with the shape of the anode 24 and cathode 26 electrodes, by allowing the gel to migrate through this layer and contact the full area of the electrodes when the device is assembled for use.

Importantly, the occlusive ring 46 provides a barrier for gel migration so the outside surface remains relatively dry during storage if the pads are separately stored and may be designed for adhesive attachment of the pad 40 to a corresponding electrode recess 20 using adhesive material in the rings 16 during activation of the device.

The gels are preferably formulated with a viscosity range preferably between 8,000-120,000 centipoise, but this is not limited so long as the gel retains shape to be successfully assembled in the patch. The gels useful in the system may be formulated by dissolving an appropriate amount of formulated drug in a cross-linked or cross-linkable gelling agent such as HPMC (hydroxpropylmethylcellulose) such that a conductive gel of appropriate viscosity is created. Other gelling agents, such as PVP (polyvinylpyrrolidone), PEO (polyethyleneoxide), or PVA (polyvinylalcohol) can also be used. Successful gels have been formulated from a HPMC powder at 2% w/w contained in a scrim.

As packaged, the integrated iontophoresis patch of the invention is designed to contain the therapeutic material to be administered, preferably in the form of a hydrogel absorbed into the absorbent composite pads 40 and contained within the patch as manufactured. Thus, the only operation left to the user may be to open the packaging and apply the patch to an affected area sought to be treated. In this way, subjects can successfully treat themselves by simply positioning the patch on the skin using the adhesive at the desired position.

As indicated, the hydrogel absorbent pads 40 may also be separately stored in common packaging and simply applied to the patch when the package is opened. In one preferred embodiment, the dexamethasone or other corticosteroid compound is co-packaged with the patch in a shape retentive gel pad form and thereafter assembled in the patch at the time of use using an adhesive to adhere the occlusive ring to the corresponding electrode recess. Either embodiment eliminates the need for the addition of any free-flowing solution material to the system at the point of use as the system is entirely self-contained and only requires the gel or gel-containing pads to be inserted into the patch.

An important aspect of the present invention involves the ability to safely apply a higher dosage of a corticosteroid than has previously been achieved by iontophoresis. Whereas known devices have been used to apply a charged dosage between 40 and 80 mAmin, the patch of the present invention is designed to enable the administration of larger doses, i.e., >80 mAmin in a manner which remains skin-safe. Heretofore, higher applied charged dosages have been known to produce adverse effects to the skin from an electrical safety viewpoint. Dexamethasone, for example, has been known to produce side effects such as skin pigmentation changes, thinning of skin or allergic skin-sensitive reactions and the risk of these effects has been seen to increase with increasing dosage. With the patch of the present invention, however, higher applied charge dosages have been demonstrated to be quite safe.

Another option for packaging includes having a dry patch and separately positioned gel reservoirs contained on a common foldable release card. The combination of the gel into the patch with this system occurs prior to use with a simple folding mechanism. This storage and activation system is described, for example, in U.S. Pat. No. 6,745,071, which may be deemed incorporated by reference herein for any purpose.

It is an important aspect of the concept that, in addition to being able to administer a greater dosage, the preferred integrated iontophoresis patch in accordance with the present invention is preferably current regulated and able to sustain a generally constant delivery rate of the therapeutic material for longer application periods than have heretofore been used by clinicians.

It is also contemplated, however, that embodiments utilizing voltage controlled circuitry may also be devised by those skilled in the art for use in relatively longer application periods.

3. Treatment Examples

In the following examples, Example 1 shows patches in accordance with the present invention to be systemically safe, such that only a minimal amount of corticosteroid is released to the systemic blood circulation when compared to the amount released after a subcutaneous injection. Example 2 involves a cumulative irritation study which shows that patches in accordance with the present invention also do not substantially irritate a subject's skin or are skin-safe.

Example 1

Systemic Delivery Study

Purpose/Objectives:

The purpose of the study was to determine the systemic plasma exposure, absorption characteristics and elimination characteristics of the active agent Dexamethasone sodium phosphate, (DexP) when administered from either a subcutaneous injection or an iontophoretic patch in domestic swine.

Test Device:

The patch is an active (iontophoretic) drug delivery patch which employs a low-level electrical field produced by a novel power source incorporated into the patch to "drive" the drug into the body in a pain-free manner. This system has advantages over passive patches, including more rapid and controlled delivery and the ability to deliver a wider variety of drugs.

Methods:

The study entailed administration of DexP from three concurrently applied patches delivered at 150 µA, 225 µA and 300 µA over a 9 hour period in 1 male and 1 female domestic swine. Each patch contained a 10 mg/ml Dexamethasone sodium phosphate gel (2% HPMC) in the donor cell compartment, and a 0.9% saline gel (2% HPMC) in the return cell compartment. As a comparator, a subcutaneous 6 mg dose of DexP was delivered to 1 male and 1 female domestic swine. All animals were implanted with a central venous access port (Hickman catheter) prior to administration of the drug and plasma samples were obtained pre-dosing and up to 24 hours after dosing. Samples were analyzed for the presence of dexamethasone phosphate and the data tabulated and selected pharmacokinetic parameters were calculated.

Results:

Subcutaneous administration of 6 mg DexP resulted in an $AUC_{(0-12)}$, $t_{1/2}$ and Cmax of 36.4 ng·hr/ml, 0.85 hr and 28.4 ng/ml, in the male animal and resulted in an $AUC_{(0-14)}$, $t_{1/2}$ and Cmax of 60.5 ng·hr/ml, 1.50 hr and 27.3 ng/ml in the female animal. The simultaneous application of the three patches resulted in an observed $AUC_{(0-12)}$ of 2.09 ng·hr/ml in the male and 2.51 ng·hr/ml in the female. Cmax in the patch dosed animals was 0.395 ng/ml in the male and 0.365 ng/ml in the female. Insufficient values above the LOQ for the assay did not allow determination of $t_{1/2}$ after patch removal.

Discussion/Conclusion

The subcutaneous dosing and sampling regimen allowed good estimation of $AUC_{(0-14)}$, $t_{1/2}$ and Cmax. Systemic levels of dexamethasone resulting from dosing with the patch were well above the assay LOQ during the time that the patches were in place and current applied, but rapidly fell below LOQ within an hour after the patches were removed. AUC and Cmax are significantly lower in iontophoretically delivered dexamethasone as compared to subcutaneous delivery of a recognized dose for soft tissue infiltration injuries (Physician Desk Reference, 60$^{th}$ edition, pages 1931-1933). By hour 12 plasma levels of dexamethasone from the patch dosage routes were below LOQ (0.10 ng/ml). Plasma levels for both the SQ dosed animals were also below LOQ by 14 hours.

TABLE 1

Study Design

| Group Number | Number of Animals | Dose Route |
|---|---|---|
| 1 | 2 | Patch |
| 2 | 2 | SQ |

TABLE 2

Time-points for blood collection

| Co-hort | Hours after dosing (SQ or patch activation) | | | | | | | | | | | |
|---|---|---|---|---|---|---|---|---|---|---|---|---|
| Patch | | 0.5 | 1 | 3 | 5 | 8 | 9 | 9.25 | 9.5 | 10 | 12 | 14 | 24 |
| SC | 0.25 | 0.5 | 1 | 3 | 5 | | 9 | | | | 12 | 14 | 24 |

TABLE 3

General Study Data
General Study Data, Dexamethasone dosing Patch vs. subcutaneous dose

| Animal # | Sex | Dosing date | Pre-implant Wt. (kg) | Duration of blood sampling (hours) | Dose | Dose route |
|---|---|---|---|---|---|---|
| 8P167 | M | Mar. 11, 2008 | 56.0 | 24 | 6 mg | SQ |
| 8P168 | F | Mar. 11, 2008 | 57.6 | 24 | 6 mg | SQ |
| 8P171 | F | Mar. 11, 2008 | 56.2 | 24 | 1-3* | Patch |
| 8P172 | M | Mar. 11, 2008 | 53.8 | 24 | 1-3* | Patch |

*Doses are estimated per each patch

TABLE 4

Summary for Total Current Applied for Patch Application

| | Delivered Current (mA · min) | | | |
|---|---|---|---|---|
| Animal # | 150 µA | 225 µA | 300 µA | TOTAL |
| 8P171 | 83.5 | 121.7 | 162.5 | 367.7 |
| 8P172 | 69.1 | 126.6 | 162.8 | 358.5 |

TABLE 5

Pharmacokinetic parameters estimated from bioanalytical data

| Animal | Dose Route | AUC$_{(0-12)}$ (ng · hr/ml) | t½ (hr) | Cmax (ng/ml) |
|---|---|---|---|---|
| 8P171 | Patch | 2.09 | not calculated | 0.365 |
| 8P172 | Patch | 2.51 | not calculated | 0.395 |
| 8P167 | SC | 36.4 | 0.85 | 28.4 |
| 8P168 | SC | 60.5 | 1.50 | 27.3 |

Example 2

Cumulative Irritation Study

Purpose/Objectives: The purpose of this study is to examine cumulative irritation effects from 10 applications of iontophoretic patches over 21 days at three applied currents.

Test Device: The patch is a multilayer composite of tan backing material, printed electrode (silver chloride cathode, zinc anode), clear occlusive tape and foam adhesive (skin contact layer). During iontophoresis the anode and cathode layers are consumed. Once either layer is consumed drug is no longer delivered. The anode is pre-trimmed to produce known dosage amounts of drug. The unit for dosage is milliamp·minutes (mAmin), which is equal to the current multiplied by time. For example, 60 mAmin can be achieved by applying 4 mA current over 15 minutes, 1 mA over 60 minutes, and so on. In general, 1 mg of drug is iontophoretically administered per 60 mAmin. Hydrogels are contained in non-woven pads maintained separate from the patch until application to the animal. Each pad is 12.5 cm$^2$ in which 1.54 grams of hydrogel is applied and maintained in a humidified environment. Prior to application, the active donor reservoir pad containing 10 mg/ml Dexamethasone sodium phosphate in a 2% HPMC hydrogel is removed from a Petri dish and transferred to the patch. A similar hydrogel pad (containing normal saline rather than dexamethasone) was applied to the counter reservoir pad.

Methods: Patches were applied successfully every other day to all 6 animals for the planned treatment period of 20 days, with the exception of the first day application of the 150 µA patch. HOBO (electrical) monitoring was performed for all patches and data tabulated daily. Skin tests with a grading score from 0-4 were performed at baseline prior to patch application and daily for the duration of the study. The patch sites were evaluated within 2 hours of patch removal on patch application days. At the penultimate patch application day, the recovery of applied drug was determined by measuring residual dexamethasone in the patch preparation pouch and in the gel pad at removal. These samples were extracted for total dexamethasone recovery and these data compared to amount of drug added during the imbibing procedure were tabulated. On the final day of patch application, plasma samples were taken and the resulting systemic exposure of dexamethasone (AUC and Cmax for each of the animals) was determined and tabulated. Three days after the final patch application, the animals were sacrificed and skin samples taken from the drug-gel and the return gel (NaCl) sites as well as control skin. These samples were fixed, stained, slides prepared and sent to the Study Pathologist for evaluation Results:
Patch application for all three current levels was performed successfully. There was a patch malfunction for the first application of the 150 µA patches resulting in changing to a new site for applications 2-10 and a cumulative evaluation of only 9 cycles for this applied current. The HOBO systems captured and recorded time vs. current information for all sites with only 1 failure for the total of 170 patch applications. This current application was estimated by the periodic FLUKE voltage measurements and was deemed to be within 10% of the target voltage. For all 170 patch applications only 9 resulted in delivery of <80% of the target mA·min AUC (2 of 54 for the 150 µA group, 4 of 60 for the 225 µA group and 5 of 60 for the 300 µA group). These observations where the delivered current was <80% of expected were either due to problems with adhesion or mechanical detachment of the patches due to activity of the animal.

Skin irritation evaluation in the drug-gel or return gel sites resulted in the vast majority of observations at 0 with a low frequency (<1%) of scores of 1 for erythema and only scores of 0 for edema.

Systemic plasma exposure of the animals to Dexamethasone was determined during the final patch application. The Cmax and AUC for the animals was 0.583±0.498 ng/ml and 4.01±2.86 ng·hr/ml respectively.

Microscopic evaluation of the patch sites (drug-gel and return-gel sites), one control skin site, and non-target organs with gross lesions from each of the six pigs showed no appreciable skin changes ascribable to the patches at the drug-gel or at the return-gel sites.

Discussion/Conclusion:

The specific aims of this study were to evaluate the cumulative effect of dexamethasone patches in skin irritation over 10 repeated applications. In addition an evaluation of the final systemic exposure of the animals to dexamethasone was evaluated as well as the recovery of Dexamethasone from the patches after the completion of application. Patch adhesion issues were observed over the 10 cycles, but were manageable throughout the study resulting in overall cumulative current delivery for all three patches which was within acceptable range of the target. Skin irritation results from either the drug-gel or return-gel sites showed no significant erythema scores and no edema observed with any of the three levels of applied current. Microscopic histological evaluation also showed no treatment-related effect of the patches at either the drug-gel or return-gel sites.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A method for treating site specific inflammatory pain in a patient, the method comprising:
    (a) applying an integrated transdermal patch to a skin surface of a patient comprising a selected site of inflammatory pain, wherein the integrated transdermal patch comprises an electrode assembly disposed between a flexible backing layer and a barrier layer and is configured for transdermal delivery of a charged corticosteroid from a reservoir that comprises a formulated corticosteroid composition consisting of:
        the charged corticosteroid;
        a gel; and
        an absorbent pad disposed within the barrier layer;
    wherein the flexible backing layer, the barrier layer and the charged corticosteroid the and the absorbent ad of the formulated corticosteroid composition are each disposed against and directly contact said skin surface; and
    (b) using said applied transdermal patch to deliver a quantity of the charged corticosteroid through said skin surface in a time period between about 6 hours and about 20 hours, wherein the transdermal delivery is facilitated by iontophoresis administering an applied charge dose that exceeds 80 mAmin;
    to treat said patient for site specific inflammatory pain.

2. A method as in claim 1 wherein the charged corticosteroid is selected from the group consisting of dexamethasone salts and betamethasone salts and combination thereof.

3. A method as in claim 2 wherein the charged corticosteroid is selected from the group consisting of dexamethasone sodium phosphate and betamethasone sodium phosphate and combinations thereof.

4. A method as in claim 1 wherein the total iontophoretic current is current regulated and less than 1 mA on average.

5. A method as in claim 1 wherein current density during delivery is limited to less than 100 µA/cm$^2$ of electrode.

6. A method as in claim 1 wherein the formulated corticosteroid composition has a charged corticosteroid concentration equal or greater than 0.5%.

7. A method as in claim 6 wherein the formulated corticosteroid composition has a charged corticosteroid concentration equal or greater than 1.0%.

8. A method as in claim 1 wherein the iontophoretic power is supplied by a combination device dedicated to delivery of a corticosteroid.

9. A method as in claim 1 wherein said delivery of said charged corticosteroid does not substantially irritate a subject's skin.

10. A method as in claim 1 wherein said delivery of said charged corticosteroid results in a skin erythema score of 2.00 or less.

11. A method as in claim 1 wherein said delivery of said charged corticosteroid results in a skin erythema score of 1.0 or less.

12. A method as in claim 1 wherein said time period is between about 8 and about 12 hours.

13. A method as in claim 1 wherein said time period is between about 8 and about 10 hours.

14. A method as in claim 1 wherein said gel is a hydrogel.

15. A method as in claim 14 wherein said hydrogel has a viscosity in the range between about 8,000 centipoise and 120000 centipoise.

16. A method as in claim 14 wherein said hydrogel includes HPMC (hydroxypropylmethylcellulose).

17. A method as in claim 1 wherein said corticosteroid composition is formulated for delivery of said charged corticosteroid from a patch cathode.

18. A method as in claim 1 wherein said patch is activated by a user by opening packaging and applying the patch to an area sought to be treated.

19. A method according to claim 1, wherein the patch comprises a cathode and anode and the formulated corticosteroid composition is in contact with the cathode.

20. The method according to claim 1, wherein the charged corticosteroid is present as a negatively charged ion.

21. The method according to claim 1, wherein the absorbent pad comprises an occlusive peripheral ring layer comprising an adhesive and defining a permeable region of the pad.

22. The method according to claim 21, wherein the permeable region of the pad is disposed adjacent to an electrode and the permeable region is shaped to align with the shape of the electrode.

23. The method according to claim 1, wherein the electrode assembly is disposed against the flexible backing layer, the barrier layer and the absorbent pad.

24. The method according to claim 1, wherein the reservoir comprises a recessed area defined by an adhesive border in the barrier layer, wherein the recessed area is occupied by the formulated corticosteroid composition.

25. A method for treating site specific inflammatory pain in a patient, the method comprising:
(a) applying a transdermal iontophoresis patch to a skin surface of a patient comprising a selected site of inflammatory pain, wherein the transdermal patch comprises an electrode assembly disposed between a flexible backing layer and a barrier layer, and wherein the transdermal patch is a combination device configured for and dedicated exclusively to transdermal delivery of a formulated charged corticosteroid for the site specific treatment of inflammatory pain, wherein said iontophoresis patch comprises a reservoir comprising a formulated corticosteroid composition consisting of:
the charged corticosteroid;
a gel; and
an absorbent pad disposed within the barrier layer;
wherein the flexible backing layer, the barrier layer and the charged corticosteroid, the gel and the absorbent pad of the formulated corticosteroid composition are each disposed against and directly contact said skin surface; and
(b) using said applied transdermal patch to deliver a quantity of the charged corticosteroid through said skin surface by delivering an applied charge dose that exceeds 80 mAmin in a time period of at least about 6 hours;
to treat said patient for site specific inflammatory pain.

26. A method for transdermally treating site-specific inflammatory pain in a patient, the method comprising:
(a) applying a transdermal iontophoresis patch to a skin surface of a patient comprising a selected site of inflammatory pain, wherein the transdermal iontophoresis patch comprises an electrode assembly disposed between a flexible backing layer and a barrier layer containing a therapeutic formulation consisting of one or more charged corticosteroid compounds, a gel and an absorbent pad disposed within the barrier layer;
wherein the flexible backing layer, the barrier layer and the one or more charged corticosteroid compounds the gel and the absorbent pad of the formulated corticosteroid composition are each disposed against and directly contact said skin surface; and
(b) using said applied transdermal patch to deliver a clinically effective quantity of the one or more charged corticosteroid compounds through the said skin for a time period of about 6 hours or more;
to treat said patient for site-specific inflammatory pain.

27. A method as in claim 26 wherein the one or more charged corticosteroid compounds comprise a corticosteroid selected from the group consisting of dexamethasone salts and betamethasone salts and combinations thereof.

28. A method as in claim 27 wherein the one or more charged corticosteroid compounds comprise a corticosteroid selected from the group consisting of dexamethasone sodium phosphate and betamethasone sodium phosphate and combinations thereof.

29. A method as in claim 26 wherein the concentration of one or more charged corticosteroid compounds in the therapeutic formulation is equal or greater than 0.5%.

30. A method as in claim 29 wherein the concentration of one or more charged corticosteroid compounds in the therapeutic formulation is equal or greater than 1.0%.

31. A method as in claim 26 wherein said delivery of said one or more charged corticosteroid compounds results in a skin erythema score of 2.00 or less.

32. A method as in claim 26 wherein said time period is between about 6 and about 12 hours.

33. A method as in claim 26 wherein said transdermal patch delivers a quantity of one or more charged corticosteroid compounds averaging greater than one milligram.

34. A method for treating site specific inflammatory pain in a patient, the method comprising:
(a) providing an integrated iontophoretic transdermal patch comprising an electrode assembly disposed between a flexible backing layer and a barrier layer, and a reservoir comprising a therapeutic agent in the form of a formulated corticosteroid composition, wherein the formulated corticosteroid composition consists of:
(i) a viscous gel; and
(ii) a charged corticosteroid; and
(b) applying said transdermal patch to a skin site of said patient to iontophoretically deliver a quantity of the charged corticosteroid via application of an iontophoretic current through the skin surface of said patient overlying a selected site in a time period between about 6 hours and about 20 hours wherein said patch delivers said charged corticosteroid to treat said patient for site specific inflammatory pain, wherein the flexible backing layer, the barrier layer, the viscous gel and the charged corticosteroid are each disposed against and directly contact the skin surface of a patient.

35. A method according to claim 34, wherein the patch comprises a cathode and anode and the formulated corticosteroid composition is in contact with the cathode.

36. The method according to claim 34, wherein the charged corticosteroid is present as a negatively charged ion.

* * * * *